(12) United States Patent
Lai et al.

(10) Patent No.: US 9,017,794 B1
(45) Date of Patent: Apr. 28, 2015

(54) INTEGRATED PLASMONIC ENHANCED FLUORESCENCE FOR SENSOR APPLICATION

(71) Applicant: Secrectary of the Department of the Navy, Washington, DC (US)

(72) Inventors: William W. Lai, Ridgecrest, CA (US); Lee R. Cambrea, Ridgecrest, CA (US); Alfred J. Baca, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 33 days.

(21) Appl. No.: 13/677,492

(22) Filed: Nov. 15, 2012

Related U.S. Application Data

(60) Provisional application No. 61/562,250, filed on Nov. 21, 2011.

(51) Int. Cl.
  *G01N 21/64* (2006.01)
  *B32B 27/00* (2006.01)

(52) U.S. Cl.
  CPC ............... *G01N 21/64* (2013.01); *B32B 27/00* (2013.01)

(58) Field of Classification Search
  None
  See application file for complete search history.

(56) References Cited

U.S. PATENT DOCUMENTS

| | | | | |
|---|---|---|---|---|
| 5,479,070 | A * | 12/1995 | Murakami | 313/499 |
| 5,847,506 | A * | 12/1998 | Nakayama et al. | 313/504 |
| 5,853,795 | A * | 12/1998 | Oh et al. | 427/64 |
| 6,130,001 | A * | 10/2000 | Shi et al. | 428/690 |
| 6,678,016 | B1 * | 1/2004 | Hanaoka | 348/841 |
| 6,818,733 | B2 * | 11/2004 | Yamazaki et al. | 428/917 |
| 2002/0033665 | A1* | 3/2002 | Yamazaki et al. | 313/504 |
| 2002/0055239 | A1* | 5/2002 | Tuominen et al. | 438/466 |
| 2002/0175619 | A1* | 11/2002 | Kita et al. | 313/504 |
| 2003/0127974 | A1* | 7/2003 | Miyazawa | 313/504 |
| 2004/0067339 | A1* | 4/2004 | Gandon et al. | 428/141 |
| 2005/0228491 | A1* | 10/2005 | Snyder et al. | 623/1.46 |

FOREIGN PATENT DOCUMENTS

EP  1416303 A2 *  5/2004

OTHER PUBLICATIONS

Hwang et al. "Surface Plasmon Polariton Enhanced Fluorescence from Quantum Dots on Nanostructured Metal Surfaces"; Nano Lett., 2010, 10, pp. 813-820.*
Anker et al. "Biosensing with plasmonic nanosensors"; Nature Materials, vol. 7, Jun. 2008, pp. 442-453.*
Hou, et al., Reaction of 2,3-dichloro-5,6-dicyanopyrazine with amines. Dyes and Pigments 22 (1993) 57-68.
Maseru Matsuoka, Syntheses & spectral properties of 2,3,7,8-tetracyano 5,10-dihydrodipyrazino[2,3-b:2',3'-e]pyrazine, J. Hetero. Chem. Mar.-Apr. 1997.
Baca, et al. molded plasmonic crystals for detecting & spatially imaging surface bound species by surface-enhanced Raman scattering. APL 94 243109 (2009).

* cited by examiner

*Primary Examiner* — David Sample
*Assistant Examiner* — Donald M Flores, Jr.
(74) *Attorney, Agent, or Firm* — Charlene A. Haley

(57) ABSTRACT

A plasmonic array and methods of fabricating having a substrate, a layer of elastomeric material cured in nanowell or nanopost features, a fluorescent layer, and a plasmonic metal layer on top.

11 Claims, 5 Drawing Sheets

INTEGRATED PLASMONIC ENHANCED FLUORESCENCE FOR SENSOR APPLICATION

CROSS-REFERENCE TO RELATED APPLICATIONS

This is a non-provisional patent application of, claiming the benefit of, parent application Ser. No. 61/562,250 filed on Nov. 21, 2011, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a method of increasing limit of detection of fluorescent based sensors by incorporating a plasmonic structure.

Figure 1:
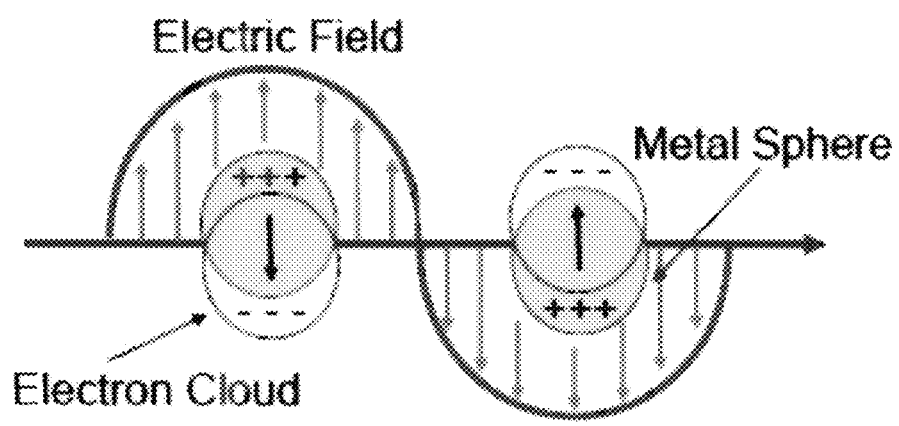
FIGS. 1 and 2 are perspective views of localized surface plasmon resonance. Light interacts with features smaller than the incident wavelength causing plasmons to oscillate locally around the feature with a frequency known as the LSPR. When an analyte is in close proximity to these oscillating plasmons, signal enhancements can occur as shown in FIG. 2, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to methods of increasing limit of detection of fluorescent based sensors by incorporating a plasmonic structure.

We can imprint nanowells in a variety of materials provided that they are soluble in common organic solvents. Solvents that are too harsh (caustic, corrosive) in nature are not compatible with our current stamp technology. The family of fused pyrazines first reported by Matsuoka is both highly fluorescent and easily functionalizable. By changing the functional groups at the 9 and 10 positions the electronic and physical properties can be tuned to meet desired specifications.

References: Dyes and Pigments 22(1), 57-68, 1993; Journal of Heterocyclic Chemistry 34(2), 653-657, 1997; applied Physics Letters, 93, 24309-01 2009.

Provides a pathway for the miniaturization of fluorescence sensors by combining the active fluorescence layer with the ability for self signal enhancement.

The trend in sensor sizes continues to trend towards smaller and smaller. The unfortunate corollary to this fact is that the probability of the desired analyte registering with the sensor also decreases with diminishing size. In order to continue this trend towards further minimization, any response that an analyte does cause has to be enhanced/increased to a level that can be registered by the device. While the sensor and amplifier are usually two separate entities, what we are disclosing is the combination of the two, into one active fluorescence layer that also serves to self enhance the signal responses. This will allow for the further minimization without the expense of signal loss. Nanoscale wells, either normal or conical in conformity, can enhanced amplify signal response by surface plasmonic harmonics. This can be further tuned based on the spectrum range of interest. Although there are other fluorescence systems, the completely organic nature of the family of compounds that we are disclosing is readily functionalized so that the wells can be fabricated using common organic solvents. These materials are also resistant to oxidation and thermally stable to 250° C.

The base dihydro fused pyrazine compound is made as described in Journal of Heterocyclic Chemistry (1997), 34(2), 653-657. From this root compound, a wide range of compounds can be made by functionalizing at the 9 and 10 positions (see below).

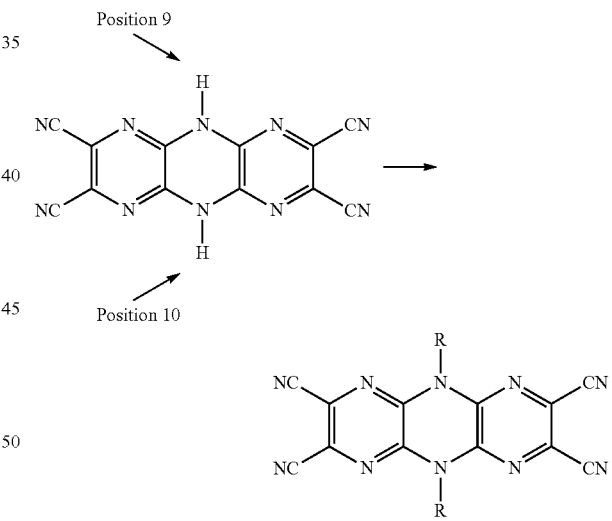

Physical properties, including thermal stability and solubility can be tuned, as well as electronic properties, including conductivity can be adjusted by inducing specific packing. Any changes made to the functionality at the 9 and 10 positions have no effect on the fluorescence, since the degree of conjugation of the pyrazine cores are consistent throughout the family of compounds. Preliminary work on imprinting nanowells have already been performed on similar materials. Several fused pyrazine derivatives have also been made and tested for redox stability and solubility.

Figure 4:
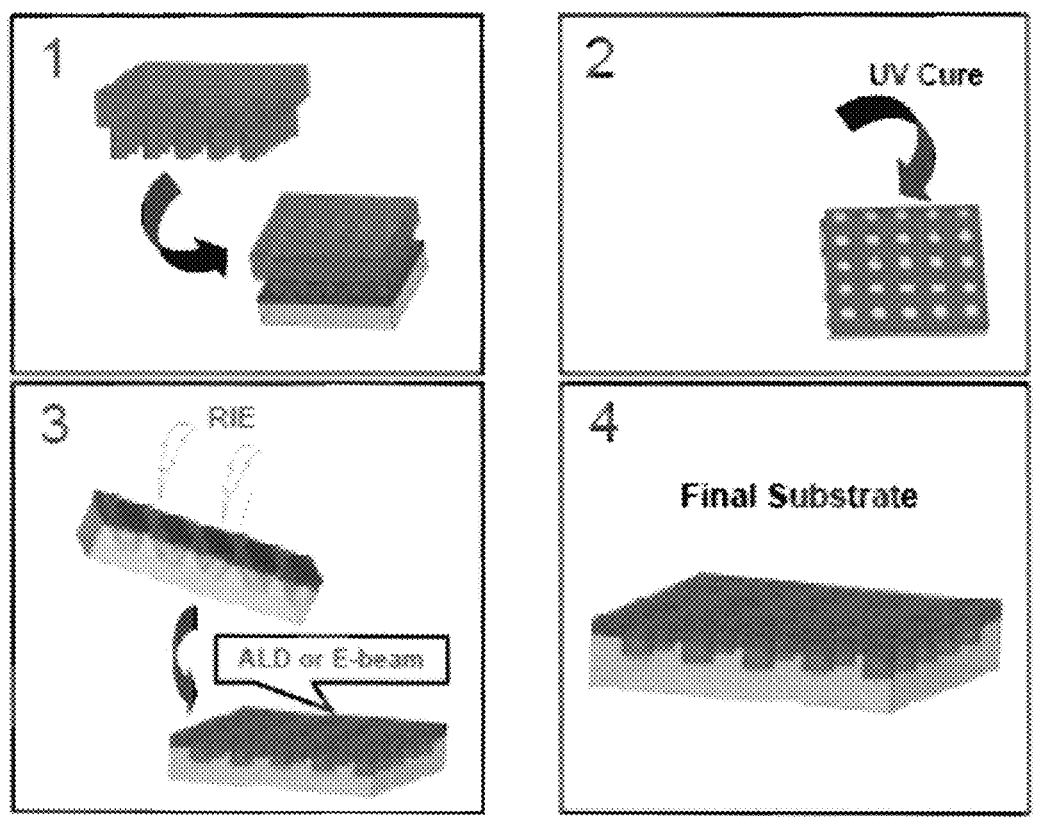
FIG. 4 is a schematic illustration showing perspective views of plasmonic substrate preparation, according to embodiments of the invention.
Figure 5:
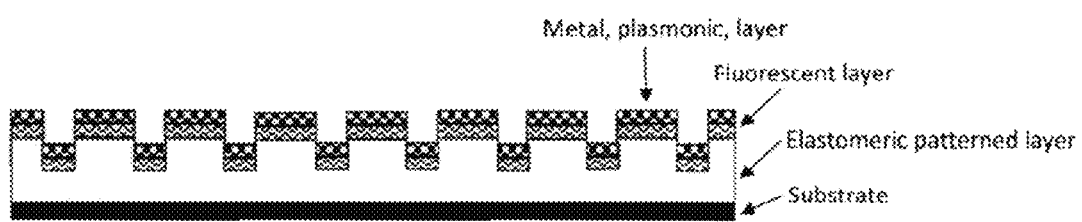
FIG. 5 shows a cross-sectional view of the completed substrate, according to embodiments of the invention.

The final substrate will be fabricated in a three-step process: 1) an elastomeric material is patterned and cured in a predefined template with the desired features (nanowells or nanoposts); 2) a fluorescent compound is deposited over the predefined template; 3) deposition of a plasmonic active metal including, but not limited to, Au and Ag onto the device completes the process. FIG. 4 shows the fabrication process. FIG. 5 shows the completed device with defined layers.

Figure 2:
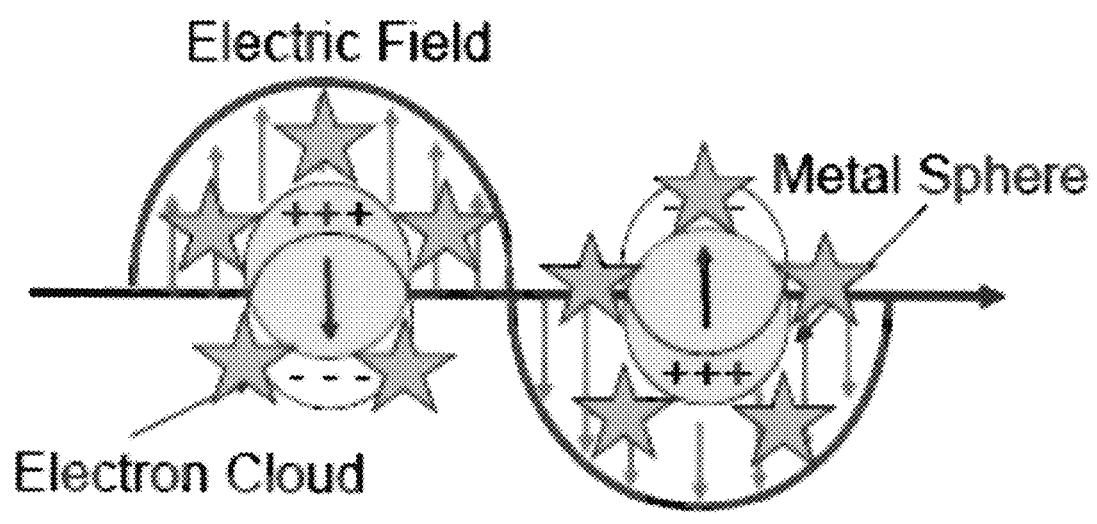

Plasmonics:

FIGS. 1 and 2 are perspective views of localized surface plasmon resonance. Light interacts with features smaller than the incident wavelength causing plasmons to oscillate locally around the feature with a frequency known as the LSPR. The features must be smaller than the wavelength of incident light for coupling to occur (e.g. traditional fluorescence=250-800 nanometers). When an analyte is in close proximity to these oscillating plasmons signal enhancements can occur.

Figure 3:
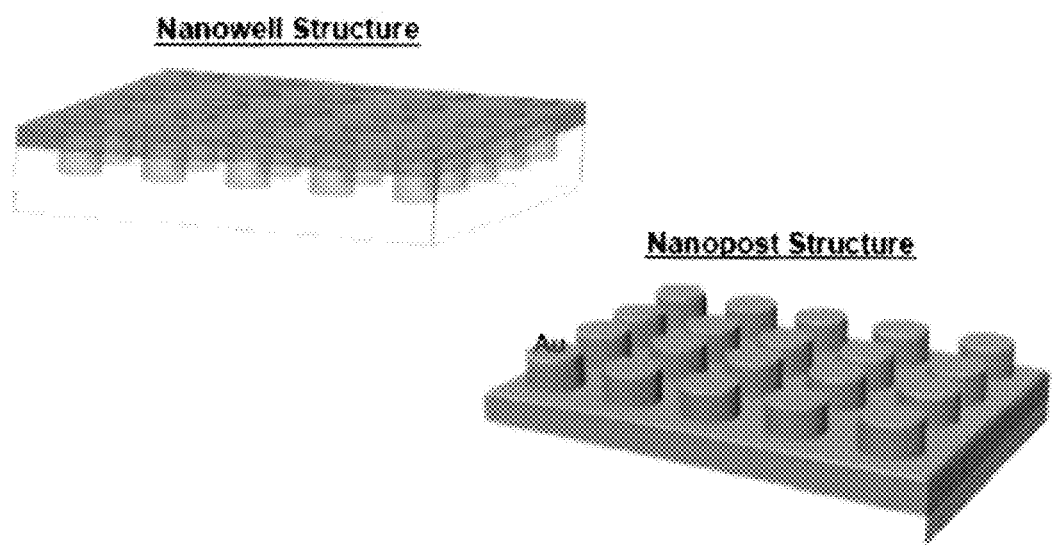
FIG. 3 is perspective views showing examples of plasmonic array structures illustrating nanowell and nanopost structures, according to embodiments of the invention.

FIG. 3 show examples of plasmonic array structures illustrating nanowell and nanopost structures. The localized surface plasmon resonance wavelength depends upon the size of the structures. For sensor applications, the structure size is chosen where the localized surface plasmon resonance best matches the fluorescence wavelength.

FIG. 4 is a schematic illustration of the preparation of a plasmonic substrate.

FIG. 5 is a cross section view of the completed device showing the different layers.

Embodiments of the invention generally relate to plasmonic fluorescence devices including, a rigid or flexible substrate, a first elastomeric layer with a predefined template having nanoposts and/or nanowells, a second layer having at least one fluorescent compound associated with the first elastomeric layer, and a third layer having one optically transparent metal layer associated with the second fluorescent layer.

Embodiments of the invention generally relate to fluorescence sensors including, at least one active fluorescence layer and at least one metal layer, which serves to self-enhance signal responses to complete the sensor, and at least one nanowell and/or nanopost structure array associated with the fluorescence layer to enhance the fluorescent layer signal response by surface plasmonic harmonics, where the nanowells and/or nanoposts are sized based on the fluorescent layer ranging from about 250 nm to about 800 nm.

In embodiments, the first elastomeric layer material is made of a polymer including silicone or Teflon structured with a predefined template of nanowells, nanoposts or a combination thereof. In embodiments, the fluorescent layer is made of a material selected from the group consisting of fluorescent compounds including fused pyrazine, polyimidizole, polythiophene, and any combination thereof. In embodiments, the optically transparent metal layer is made of material selected from the group consisting of plasmonic active metals including Au, Ag, Cu, Pd, Pt, Al, and any combination thereof. In embodiments, the substrate is selected from the group consisting of glass, plastic, Si, metal, and oxide. In embodiments, the plasmonic device is associated with a fluorescence sensor. In embodiments, the second fluorescent layer has a thickness ranging from about 50 nm to about 400 nm. In other embodiments, the metal layer has a thickness ranging from about 10 nm to about 50 nm. In embodiments, the structures are either normal or have conical conformity.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A plasmonic fluorescence device, consisting of:
   a rigid or flexible substrate;
   a first elastomeric layer with a predefined template having nanoposts and/or nanowells;
   a second layer having at least one photoluminescent-fluorescent compound associated with said first elastomeric layer; and
   a third layer having one optically transparent plasmonic active metal layer associated with said second layer, wherein each said layer(s) is conformally stacked upon each other and substantially maintains the shape and size of said nanoposts and/or nanowells.

2. The device according to claim 1, wherein said first elastomeric layer material is made of a polymer including silicone or Polytetrafluoroethylene structured with a predefined template of nanowells, nanoposts or a combination thereof.

3. The device according to claim 1, wherein said fluorescent layer is made of a material selected from the group consisting of fluorescent compounds including fused pyrazine, polyimidizole, polythiophene, and any combination thereof.

4. The device according to claim 1, wherein said optically transparent metal layer is made of material selected from the group consisting of plasmonic active metals including Au, Ag, Cu, Pd, Pt, Al, and any combination thereof.

5. The device according to claim 1, wherein said plasmonic device having fluorescent application.

6. The device according to claim 1, wherein said second layer has a thickness ranging from about 50 nm to about 400 nm.

7. The device according to claim 1, wherein said metal layer has a thickness ranging from about 10 nm to about 50 nm.

8. A fluorescence sensor, consisting of:
   a rigid or flexible substrate;
   at least one active photoluminescent-fluorescence layer and at least one metal layer, which serves to self-enhance signal responses to complete said sensor; and
   at least one nanowell and/or nanopost structure array associated with said fluorescence layer to enhance said fluorescent layer signal response by surface plasmonic harmonics, wherein said nanowells and/or nanoposts range from about 250 nm to about 800 nm in diameter, wherein each said layer(s) is conformally stacked upon each other and substantially maintains the shape and size of said nanoposts and/or nanowells.

9. The sensor according to claim 8, wherein said structures are either normal or have conical conformity.

10. A plasmonic fluorescence system to detect analytes, comprising
    a rigid or flexible substrate;

a first elastomeric layer with a predefined template having nanoposts and/or nanowells;

a second layer having at least one photoluminescent-fluorescent compound associated with said first elastomeric layer; and a third layer having one optically transparent plasmonic active metal layer associated with said second layer, wherein each said layer(s) is conformally stacked upon each other and substantially maintains the shape and size of said features being nanoposts and/or nanowells, and at least one external light source producing incident light, wherein said incident light interacts with said nanoposts and/or nanowells, that are smaller than the wavelength of the incident light, causing plasmons to oscillate locally around the nanoposts and/or nanowells to produce enhancement of an analyte(s) signal in the form of fluorescence when an analyte is in close proximity to these oscillating plasmons, wherein said features range from about 250 nm to about 800 nm in diameter, wherein incident light couples with said features to produce enhancement of analyte(s) signal in the form of fluorescence.

11. An analyte sensor system, comprising:

providing at least one external light source producing incident light, wherein said incident light interacts with said nanoposts and/or nanowells;

providing at least one analyte for detection;

at least one active photoluminescent-fluorescence layer and at least one metal layer, which serves to self-enhance signal responses to complete said sensor; and at least one feature being nanowell and/or nanopost structure array associated with said fluorescence layer to enhance said fluorescent layer signal response by surface plasmonic harmonics, wherein said features range from about 250 nm to about 800 nm in diameter, wherein each said layer(s) is conformally stacked and substantially maintains the shape and size of said nanoposts and/or nanowells.

* * * * *